United States Patent
Lu et al.

(10) Patent No.: US 7,387,432 B2
(45) Date of Patent: Jun. 17, 2008

(54) SLIDABLE SECURING DEVICE FOR A MIXER TO ALLOW COMMUNICATION BETWEEN A MIXER HOUSING AND A MIXER INLET PORTION OF THE MIXER

(75) Inventors: Li-Chuan Lu, Hsin-Tein (TW); Phillip Phung-I Ho, 2780 State St., Suite No. 7, Santa Barbara, CA (US) 93105

(73) Assignees: Meditech International Ltd.-Samoa, Apia (WS); Phillip Phung-I Ho, Santa Barbara, CA (US)

( * ) Notice: Subject to any disclaimer, the term of this patent is extended or adjusted under 35 U.S.C. 154(b) by 76 days.

(21) Appl. No.: 11/546,218

(22) Filed: Oct. 11, 2006

(65) Prior Publication Data

US 2008/0089173 A1    Apr. 17, 2008

(51) Int. Cl.
  *B01F 5/06*   (2006.01)
(52) U.S. Cl. .................... 366/339; 222/145.6
(58) Field of Classification Search ............. 366/172.2, 366/176.1, 181.5, 325.1, 325.2, 326.1, 329.1, 366/329.2, 336–340; 222/145.5, 145.6
  See application file for complete search history.

(56) References Cited

U.S. PATENT DOCUMENTS

| | | | | |
|---|---|---|---|---|
| 4,753,536 A | * | 6/1988 | Spehar et al. | 366/339 |
| 4,767,026 A | * | 8/1988 | Keller et al. | 222/137 |
| 4,771,919 A | * | 9/1988 | Ernst | 222/134 |
| 4,846,373 A | * | 7/1989 | Penn et al. | 222/137 |
| 4,989,758 A | * | 2/1991 | Keller | 222/137 |
| 4,995,540 A | * | 2/1991 | Colin et al. | 222/132 |
| 5,033,650 A | * | 7/1991 | Colin et al. | 222/137 |
| 5,080,262 A | * | 1/1992 | Herold et al. | 222/135 |
| 5,249,709 A | * | 10/1993 | Duckworth et al. | 222/137 |
| 5,333,760 A | * | 8/1994 | Simmen | 222/137 |
| 5,413,253 A | * | 5/1995 | Simmen | 222/137 |
| 5,609,271 A | * | 3/1997 | Keller et al. | 222/145.6 |
| 5,819,988 A | * | 10/1998 | Sawhney et al. | 222/137 |
| 5,918,772 A | * | 7/1999 | Keller et al. | 222/145.6 |
| 6,443,612 B1 | * | 9/2002 | Keller | 366/307 |
| 6,530,685 B1 | * | 3/2003 | Muhlbauer et al. | 366/336 |
| 6,932,243 B2 | | 8/2005 | Keller | 222/145.6 |
| 7,316,330 B2 | * | 1/2008 | Muller et al. | 222/145.6 |
| 2007/0175921 A1 | * | 8/2007 | Keller | 222/137 |
| 2008/0029542 A1 | * | 2/2008 | Keller | 222/145.5 |

FOREIGN PATENT DOCUMENTS

| | | | |
|---|---|---|---|
| DE | 4235736 C1 | * | 3/1994 |
| EP | 232733 A2 | * | 8/1987 |
| JP | 6-226178 | * | 8/1994 |

* cited by examiner

*Primary Examiner*—Charles E Cooley
(74) *Attorney, Agent, or Firm*—Alan Kamrath; Kamrath & Associates PA

(57) ABSTRACT

A mixer includes a mixer housing provided with two annular skirts respectively extending downward to form a receiving space for communicating with an interior of the tubular housing, a mixer element having a helix extending into the tubular housing, and a mixer inlet portion with a connection plate having two top openings selectively communicating with the two openings such that components received inside the two tubes are able to be selectively forced into the interior of the tubular housing for dispensing.

8 Claims, 5 Drawing Sheets

SLIDABLE SECURING DEVICE FOR A MIXER TO ALLOW COMMUNICATION BETWEEN A MIXER HOUSING AND A MIXER INLET PORTION OF THE MIXER

BACKGROUND OF THE INVENTION

1. Field of the Invention

The present invention relates to a securing device for a mixer, and more particularly to a securing device for a mixer comprising a mixer housing and a mixer inlet portion such that after the mixer housing and the mixer inlet portion are connected via the securing device, movement of the mixer inlet portion completes alignment and communication with the mixer housing and components inside the mixer inlet portion are able to be forced into the mixer housing for dispensing.

2. Description of the Prior Art

A mixer is normally used in dental applications, with which the dentist is able to mix different components simultaneously and then forces the mixed components to wherever required. The background of the prior art can be found in U.S. Pat. No. 6,932,243 issued to Keller, where detailed description is provided to show how different components are mixed inside the mixer housing. Other information about the variations of the mixer is also available for free access so as to allow people to understand the current technologies used in the dental business.

With all the information provided, none is used to discuss how to decrease the use of the sealing film with which the components are sealed inside the mixer inlet portion before application. That is, when a user is about to use the mixer, the user peels off the sealing film on the mixer inlet portion and aligns the mixer inlet portion with the mixer housing so as to allow a plunger slidable inside the mixer inlet portion to force the components to enter the mixer housing with the influence of the mixer element. The attachment of the sealing film to the mixer inlet portion during the manufacture period increases manufacture cost. Also, the discard of the sealing film causes an environmental issue.

To overcome the shortcomings, the present invention tends to provide an improved securing device to mitigate the aforementioned problems.

SUMMARY OF THE INVENTION

The primary objective of the present invention is to provide a securing device for a mixer comprising a mixer housing and a mixer inlet portion such that after the mixer housing and the mixer inlet portion are connected via the securing device, movement of the mixer inlet portion completes alignment and communication with the mixer housing and components inside the mixer inlet portion are able to be forced into the mixer housing for dispensing.

Other objects, advantages and novel features of the invention will become more apparent from the following detailed description when taken in conjunction with the accompanying drawings.

DETAILED DESCRIPTION OF THE PREFERRED EMBODIMENT

Figure 1:
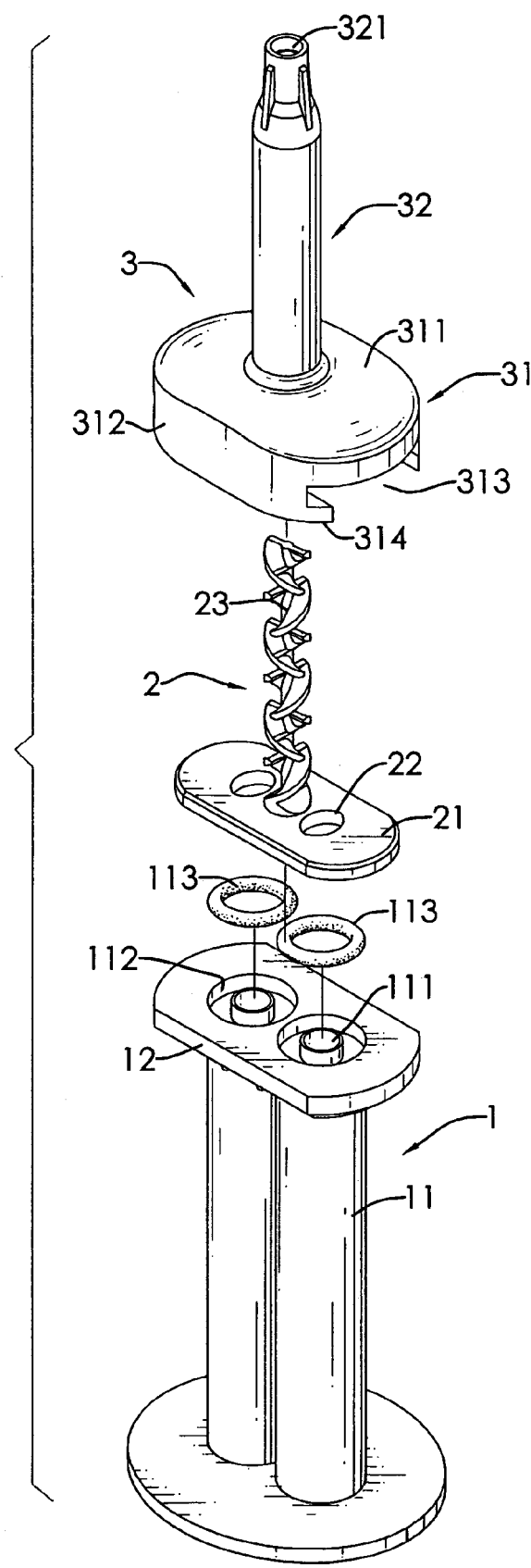
FIG. 1 is an exploded perspective view of the mixer of the present invention.

With reference to FIG. 1, it is noted that a mixer in accordance with the present invention includes a mixer inlet portion (1), a mixer element (2) and a mixer housing (3). A plunger (not shown) is also included in the mixer of the present invention when in application. However, because the plunger is conventional in the art and is not the focus of the present invention, detailed description of the plunger is omitted for clarity and to avoid confusion.

The mixer inlet portion (1) is provided with two tubes (11) for receiving therein components, each tube having a top opening (111) and a bottom opening (not numbered). A connection plate (12) is formed on a top portion of each of the two tubes (11). An annular recess (112) is defined in a top face of the connection plate (12) respectively surrounding a corresponding one of the top openings (111) of the two tubes (11) for receiving therein a seal (113) which is made of plastic. A diameter of the seal (113) is larger than a depth of the annular recess (112) such that after the seal (113) is received in the annular recess (112), a portion of the seal (113) protrudes the annular recess (112).

The mixer element (2) is provided with a base plate (21) having two openings (22) defined to respectively communicate with the two top openings (111) of the two tubes (11) of the mixer inlet portion (1). In addition, a helix (23) is integrally formed on the base plate (21) and extends upward from the base plate (21) between the two openings (22).

The mixer housing (3) has a base housing (31) and a tubular housing (32) integrally extending upward from the base housing (31). The base housing (31) has a substrate (311) and two annular skirts (312) respectively extending downward from opposed sides of the base housing (31) so as to define a receiving space (313) between the two annular skirts (312). Each annular skirt (312) is provided with a bend (314) formed on a free edge thereof. The tubular housing (32) communicates with the receiving space (313) and has an outlet (321) defined in a top portion of the tubular housing (32) and communicating with the receiving space (313).

It is noted that a width of the receiving space (313) is slightly larger than that of the base plate (21) and of the connection plate (12). A height of the receiving space (313) is substantially the same as the combination of the base plate (21) and the connection plate (12).

Figure 2:
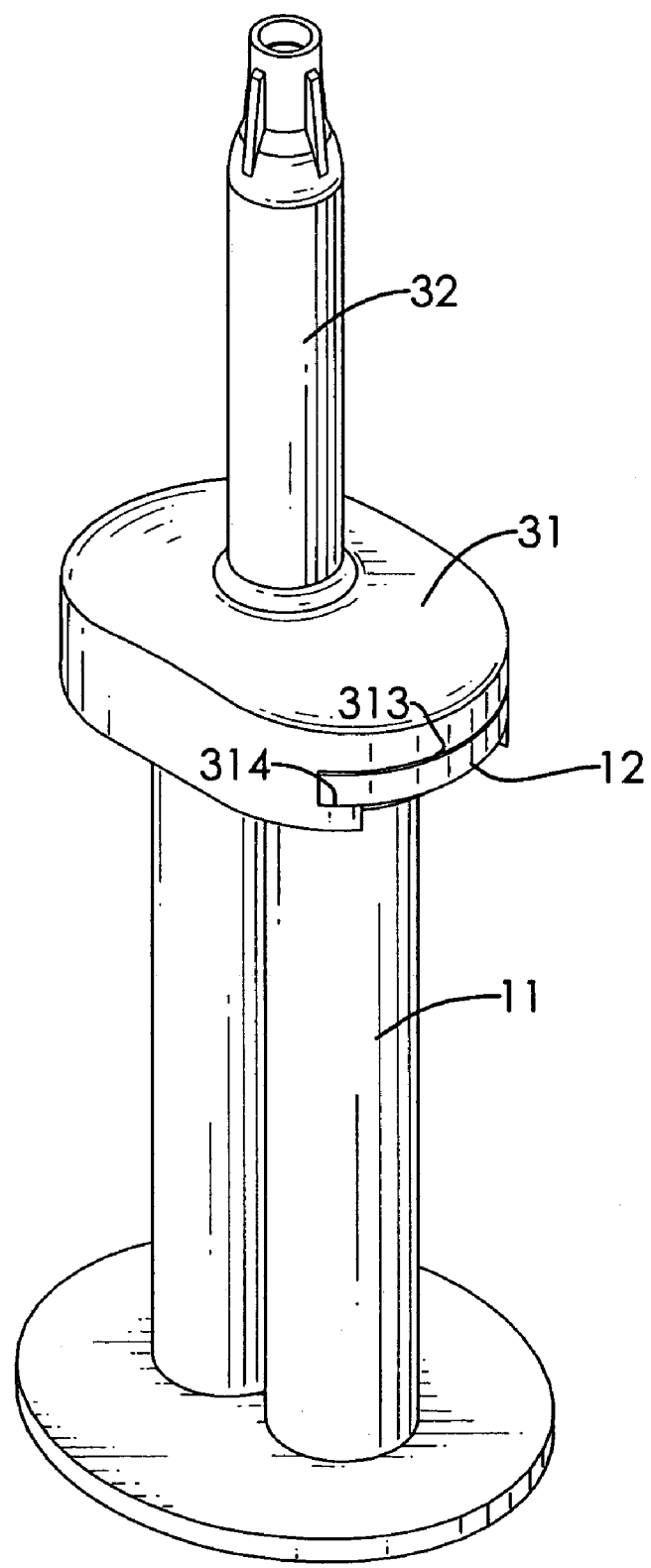
FIG. 2 is a perspective view showing the assembly of the mixer of the present invention.

With reference to FIG. 2, when the mixer of the present invention is assembled, the helix (23) of the mixer element (2) is extended into the tubular housing (32) and the base plate (21) is firmly received inside the receiving space (313). Furthermore, the connection plate (12) is also received inside the receiving space (313) with the two opposite sides of the connection plate (12) securely engaged with the two bends (314) of the base housing (31).

Figure 3:
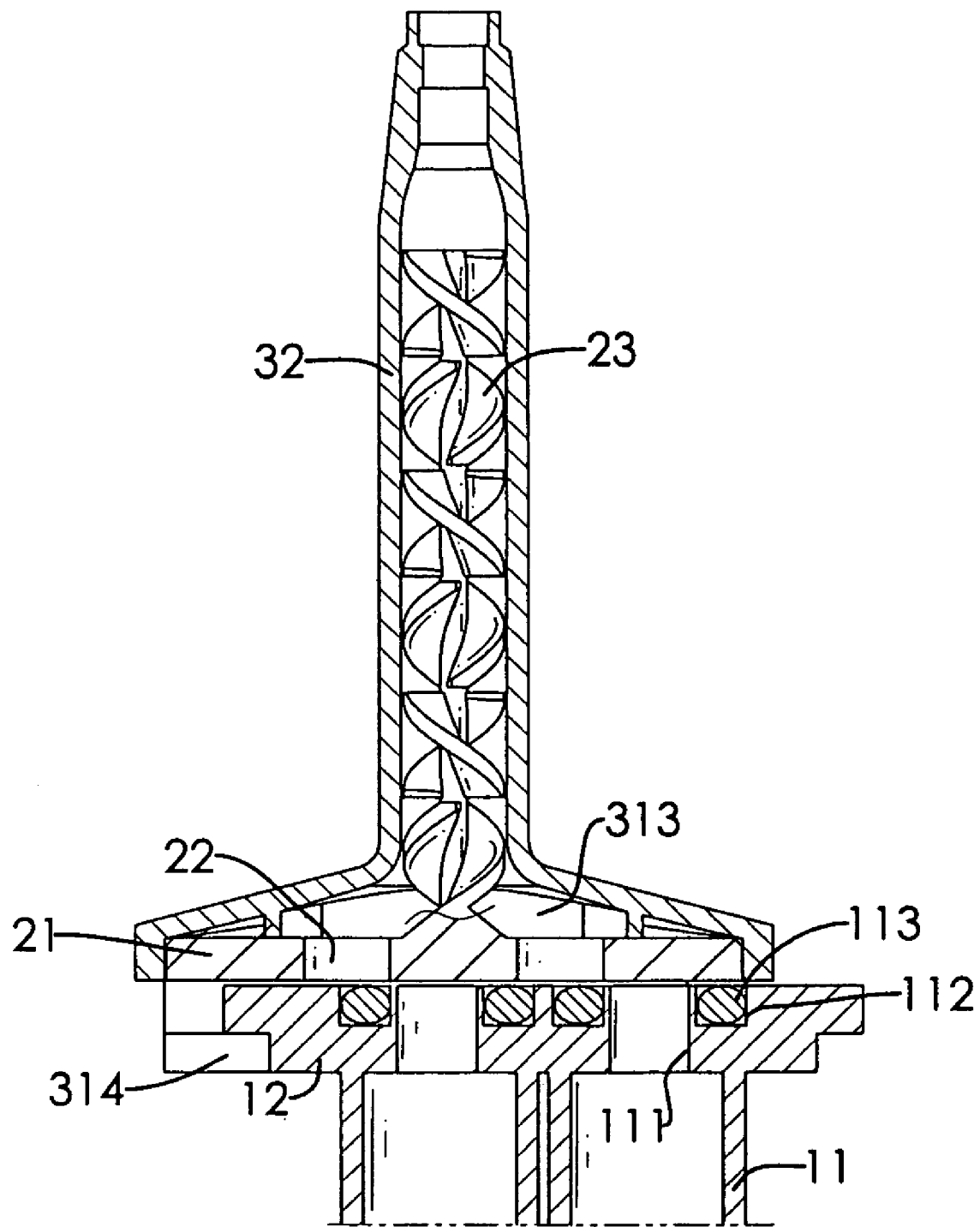
FIG. 3 is a schematic operational view showing that the communication between the mixer inlet portion and the mixer housing is blocked.
Figure 4A:
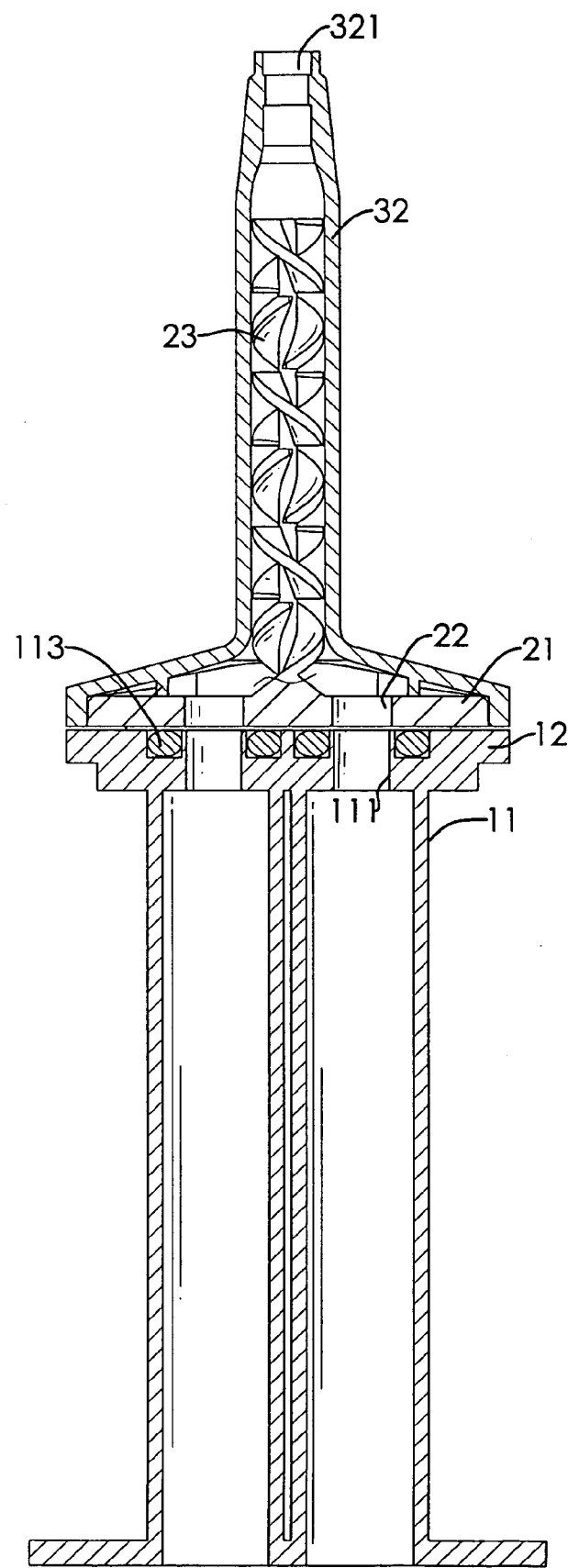
FIG. 4A is a cross sectional view showing that movement of the mixer inlet portion relative to the mixer housing completes the communication between the mixer inlet portion and the mixer housing.
Figure 4B:
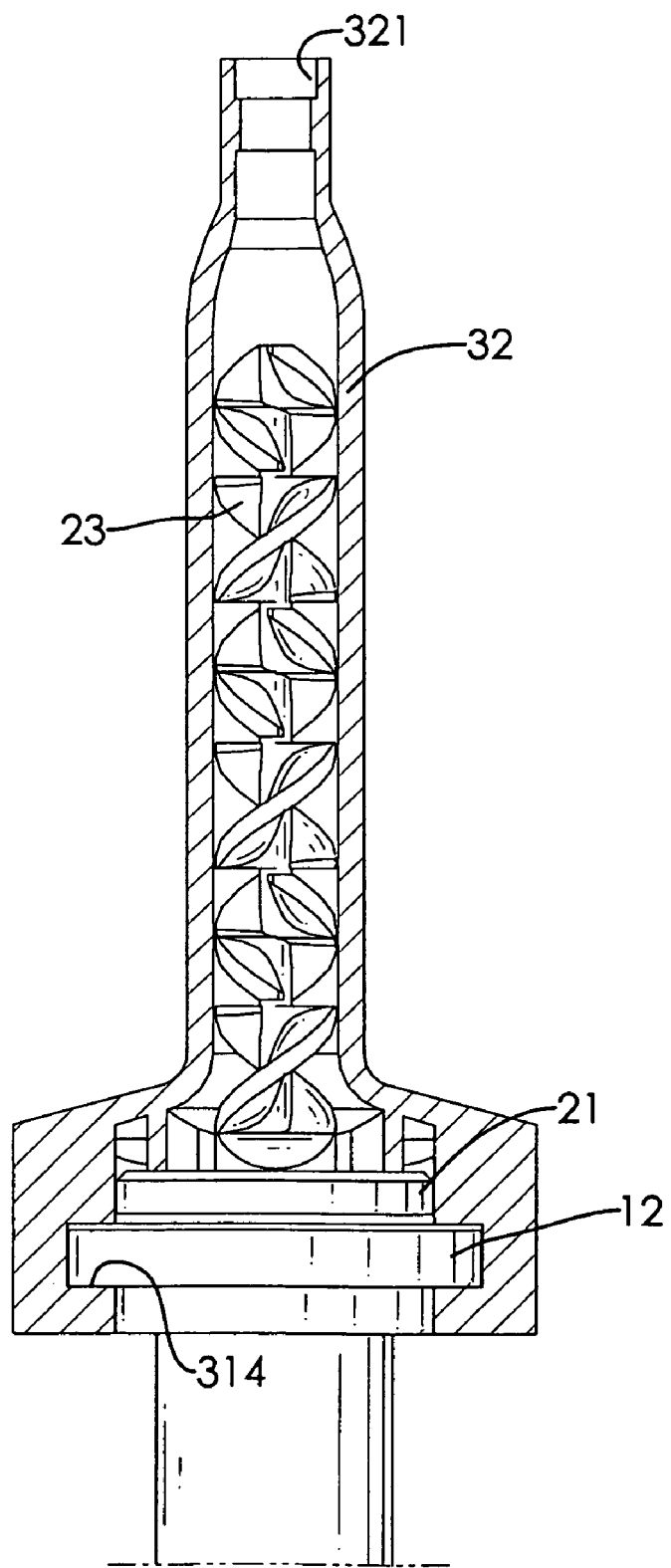
FIG. 4B is a cross sectional view from an angle different from that of FIG. 4A, wherein the mixer inlet portion is clamped by the mixer housing to maintain secure engagement between the mixer housing and the mixer inlet portion.

With reference to FIGS. 3, 4A and 4B, it is to be noted that before the application of the mixer of the present invention, the two tubes (11) are respectively filled with components of different materials and the helix (23) are received inside the tubular housing (32) with the base plate (21) received in the receiving space (313) and the two openings (22) in communication with the interior of the tubular housing (32). In the meantime, opposite sides of the connection plate (12) of the mixer inlet portion (1) are retained by the bends (314) and the connection plate (12) partially received in the receiving space (313). With only a portion of the connection plate (12) received in the receiving space (313), the two top openings (111) of the mixer inlet portion (1) are blocked by the base plate (21). That is, the two top openings (111) are mis-aligned with the two openings (22) with the two seals (113) securely sandwiched between the base plate (21) and the connection plate (12) to prevent any leakage of the components from the two tubes (11). Due to the alignment between the two top openings (111) and the two openings (22) is not completed, the components inside the two tubes (11) are not able to be forced into the tubular portion (32) via the two openings (22).

However, when the mixer of the present invention is to be applied, sliding the connection plate (12) of the mixer inlet portion (1) toward the receiving space (313) of the mixer housing (3) aligns the top openings (111) and the openings (22). That is the interior of each of the two tubes (110 communicates with the interior of the tubular housing (32) via the openings (22) and the receiving space (313). Therefore, the user is able to force the components inside each of the tubes (11) enter the interior of the tubular housing (32) for dispensing via the outlet (321) on wherever needed.

Especially, from the depiction of FIG. 4B, it is noted that a track is formed inside the receiving space (313) by the provision of the two mutually facing bends (314). Therefore, after the connection plate (12) is received inside the receiving space (313), the connection plate (12) is clamped by the two bends (314). Thus the mixer inlet portion (1) is securely connected to the mixer housing (3) with the mixer element (2) sandwiched therebetween.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A mixer comprising:
   a mixer housing provided with a substrate, a tubular housing extending upward from the substrate and having an outlet defined in a free end thereof and two annular skirts respectively extending downward from two opposed sides of the substrate so as to form a receiving space defined between the two annular skirts and communicating with an interior of the tubular housing;
   a mixer element having a base plate immovably received in the receiving space and a helix extending upward from the base plate and into the tubular housing, the base plate having two openings defined therethrough communicating with the receiving space; and
   a mixer inlet portion with a connection plate slidably received in the receiving space, two tubes each extending downward from the connection plate and having a top opening defined in a top face of the connection plate to selectively communicate with a corresponding one of the two openings of the mixer element, two annular recesses each defined in the top face of the connection plate and around a corresponding one of the two top openings to receive therein a seal which is sandwiched between the connection plate and the base plate for prevention of leakage of components received in the two tubes such that when the connection plate is in a first position, communication between the two top openings and the two openings is blocked by the connection plate and when the connection plate is slid to a second position, the two top openings communicate with the two openings and the components in the two tubes are able to be forced into the interior of the tubular housing.

2. The mixer as claimed in claim 1, each annular skirt has a bend formed on a free edge thereof so as to form a track inside the receiving space to retain the connection plate.

3. A mixer comprising:
   a mixer housing provided with a substrate, a tubular housing extending upward from the substrate and having an outlet defined in a free end thereof and two annular skirts respectively extending downward from two opposed sides of the substrate so as to form a receiving space defined between the two annular skirts and communicating with an interior of the tubular housing;
   a mixer element having a helix extending into the tubular housing; and
   a mixer inlet portion with a connection plate slidable relative to the substrate of the mixer housing, two tubes each extending downward from the connection plate and having a top opening defined in a top face of the connection plate to selectively communicate with a corresponding one of the two openings of the mixer element, two annular recesses each defined in the top face of the connection plate and around a corresponding one of the two top openings to receive therein a seal which is sandwiched between the connection plate and the base plate for prevention of leakage of components received in the two tubes such that when the connection plate is in a first position, communication between the two top openings and the two openings is blocked by the connection plate and when the connection plate is slid to a second position, the two top openings communicate with the two openings and the components in the two tubes are able to be forced into the interior of the tubular housing.

4. The mixer as claimed in claim 3, wherein the mixer element further has a base plate with the helix extending upward therefrom, the base plate has two openings defined therethrough to communicate with the receiving space.

5. The mixer as claimed in claim 4, wherein the two top openings selectively communicate with the two openings depending whether the connection plate is at the first position or at the second position.

6. The mixer as claimed in claim 3, each annular skirt has a bend formed on a free edge thereof so as to form a track inside the receiving space to retain the connection plate.

7. The mixer as claimed in claim 4, each annular skirt has a bend formed on a free edge thereof so as to form a track inside the receiving space to retain the connection plate.

8. The mixer as claimed in claim 5, each annular skirt has a bend formed on a free edge thereof so as to form a track inside the receiving space to retain the connection plate.

* * * * *